US011666768B2

(12) United States Patent
Sell et al.

(10) Patent No.: US 11,666,768 B2
(45) Date of Patent: Jun. 6, 2023

(54) ELECTRICALLY ISOLATED CONNECTOR FOR IMPLANTABLE MEDICAL DEVICES

(71) Applicant: Medtronic, Inc., Minneapolis, MN (US)

(72) Inventors: Jonathan C. Sell, Eagan, MN (US); Robert T. Sandgren, Lindstrom, MN (US); Jayesh R. Patel, Maple Grove, MN (US); Elizabeth K. Formosa, Robbinsdale, MN (US); Jeffrey Novotny, North Branch, MN (US); Wen Tan, Shoreview, MN (US); Emily Paukert, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 105 days.

(21) Appl. No.: 17/249,555

(22) Filed: Mar. 4, 2021

(65) Prior Publication Data
US 2021/0275823 A1 Sep. 9, 2021

Related U.S. Application Data

(60) Provisional application No. 62/985,026, filed on Mar. 4, 2020.

(51) Int. Cl.
*A61N 1/375* (2006.01)
*A61N 1/05* (2006.01)
(Continued)

(52) U.S. Cl.
CPC .......... *A61N 1/3752* (2013.01); *A61N 1/0551* (2013.01); *H01R 13/621* (2013.01);
(Continued)

(58) Field of Classification Search
CPC .. A61N 1/0551; A61N 1/3752; H01R 13/621; H01R 2107/00; H01R 2201/12; H01R 24/58; H01R 31/06
See application file for complete search history.

(56) References Cited

U.S. PATENT DOCUMENTS 4,357,727 A 11/1982 Mcdowell
4,583,543 A 4/1986 Peers-Trevarton
(Continued)

OTHER PUBLICATIONS

"Precision™ M8 Adapter Directions for Use", Boston Scientific Corporation, Jul. 2015.
(Continued)

*Primary Examiner* — George Manuel
(74) *Attorney, Agent, or Firm* — Patterson Thuente IP

(57) ABSTRACT

A neuromodulation adaptor configured to provide an electrical coupling between an otherwise incompatible stimulation lead and neurostimulator device, the neuromodulation adaptor including a proximal portion having a plurality of electrical conductors spaced apart at a first pitch spacing and configured to electrically engage with a corresponding plurality of electrical terminals of a neurostimulator device, and a distal portion including a stimulation lead port assembly, the stimulation lead port assembly including an upper portion and a lower portion configured to house the plurality of conductor elements and a set screw assembly, the plurality of conductor elements and set screw assembly spaced apart at a second pitch spacing and configured to electrically engage with a corresponding plurality of electrical connectors of a stimulation lead.

24 Claims, 15 Drawing Sheets

(51) Int. Cl.
    *H01R 13/621*     (2006.01)
    *H01R 24/58*     (2011.01)
    *H01R 107/00*     (2006.01)

(52) U.S. Cl.
    CPC ......... *H01R 24/58* (2013.01); *H01R 2107/00* (2013.01); *H01R 2201/12* (2013.01)

(56) References Cited

U.S. PATENT DOCUMENTS

| | | | |
|---|---|---|---|
| 4,898,173 | A | 2/1990 | Daglow et al. |
| 4,934,366 | A | 6/1990 | Truex et al. |
| 5,000,177 | A | 3/1991 | Hoffmann et al. |
| 5,413,595 | A | 5/1995 | Stutz, Jr. |
| 5,669,790 | A | 9/1997 | Carson et al. |
| 5,843,141 | A | 12/1998 | Bischoff et al. |
| 6,205,358 | B1 | 3/2001 | Haeg et al. |
| 7,083,474 | B1 | 8/2006 | Fleck et al. |
| 7,526,339 | B2 | 4/2009 | Lahti et al. |
| 7,590,451 | B2 | 9/2009 | Tronnes et al. |
| 7,736,192 | B2 | 6/2010 | Alexander et al. |
| 7,860,568 | B2 | 12/2010 | Deininger et al. |
| 7,881,783 | B2 | 2/2011 | Bonde et al. |
| 8,123,567 | B2 | 2/2012 | Kast et al. |
| 8,140,163 | B1 | 3/2012 | Daglow et al. |
| 8,180,461 | B2 | 5/2012 | Mamo et al. |
| 8,251,731 | B2 | 8/2012 | Boyd et al. |
| 8,401,649 | B2 | 3/2013 | Tronnes et al. |
| 8,525,027 | B2 | 9/2013 | Lindner et al. |
| 8,831,744 | B2 | 9/2014 | Swanson |
| 9,227,052 | B2 | 1/2016 | Robnett |
| 9,427,574 | B2 | 8/2016 | Lee et al. |
| 9,472,916 | B2 | 10/2016 | Hanson et al. |
| 9,802,038 | B2 | 10/2017 | Lee et al. |
| 9,855,423 | B2 | 1/2018 | Jiang et al. |
| 10,905,871 | B2 | 2/2021 | Nageri et al. |
| 2003/0073348 | A1 | 4/2003 | Ries et al. |
| 2003/0163171 | A1 | 8/2003 | Kast et al. |
| 2004/0176831 | A1* | 9/2004 | Gliner ............... A61N 1/0531 607/142 |
| 2008/0183236 | A1 | 7/2008 | Gerber |
| 2012/0130438 | A1* | 5/2012 | Seeley ............... H01R 24/76 607/2 |
| 2012/0203292 | A1 | 8/2012 | Deininger et al. |
| 2014/0121741 | A1 | 5/2014 | Bennett et al. |
| 2018/0078760 | A1 | 3/2018 | Lee et al. |
| 2018/0175566 | A1 | 6/2018 | Hanson et al. |
| 2019/0190215 | A1 | 6/2019 | Hanson et al. |
| 2019/0336752 | A1 | 11/2019 | Bauer et al. |
| 2019/0374776 | A1 | 12/2019 | Mishra et al. |
| 2020/0398057 | A1 | 12/2020 | Esteller et al. |

OTHER PUBLICATIONS

"Precision™ S8 Adapter Directions for Use", Boston Scientific Corporation, Jun. 2018.

Matzel et al., "Sacral Neuromodulation: Standardized Electrode Placement Technique", Neuromodulation: Technology at the Neural Interface, vol. 20, Issue 8, Jun. 12, 2017, pp. 816-824.

Spinelli et al., "Evolution of a minimally-invasive procedure for sacral neuromodulation", Chapter 18: Development of Minimally-Invasive SNS, New Perspectives in Sacral Nerve Stimulation, Martin Dunitz Ltd., Mar. 28, 2002, pp. 217-222.

Axonics Modulation Technologies, "Axonics Prepares for Introduction of its Sacral Neuromodulation System", as featured in Business in Focus, Mar. 2018, a Focus Media Group Publication.

Blok et al., "Programming settings and recharge interval in a prospective study of a rechargeable sacral neuromodulation system for the treatment of overactive bladder", Neurourology and Urodynamics, vol. 37, Issue 52, Oct. 20, 2017, pp. 1-6.

Cohn et al., "Evaluation of the axonics modulation technologies sacral neuromodulation system for the treatment of urinary and fecal dysfunction", Expert Review of Medical Devices, vol. 14, No. 1, Dec. 4, 2016, pp. 3-14.

Elterman, "The novel Axonics® rechargeable sacral neuromodulation system: Procedural and technical impressions from an initial North American experience", Neurourology and Urodynamics, vol. 37, Issue S2, Dec. 19, 2017, pp. 1-8.

U.S. Appl. No. 16/948,859, filed Oct. 2, 2020, Inventor(s): Formosa et al.

U.S. Appl. No. 16/948,857, filed Oct. 2, 2020, Inventor(s): Formosa et al.

U.S. Appl. No. 16/948,856, filed Oct. 2, 2020, Inventor(s): Sandgren et al.

* cited by examiner

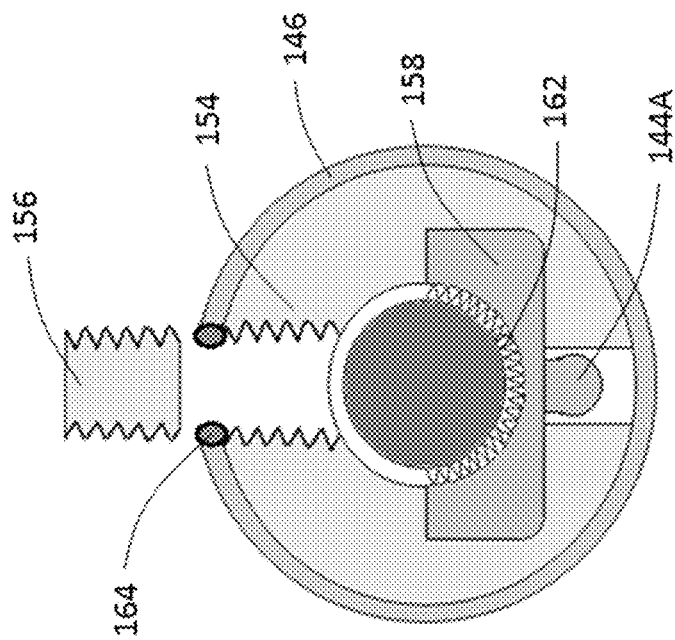
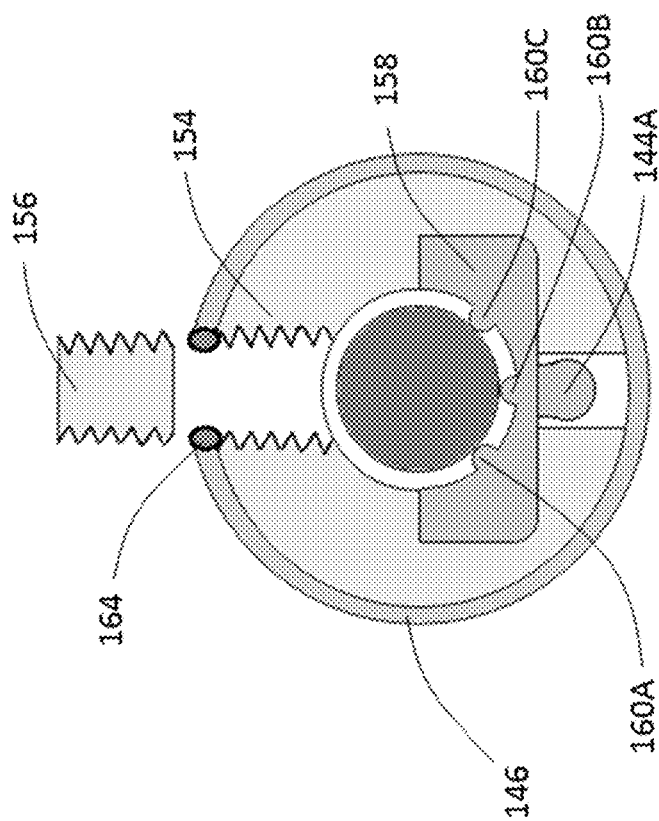
FIG. 7A
FIG. 7B

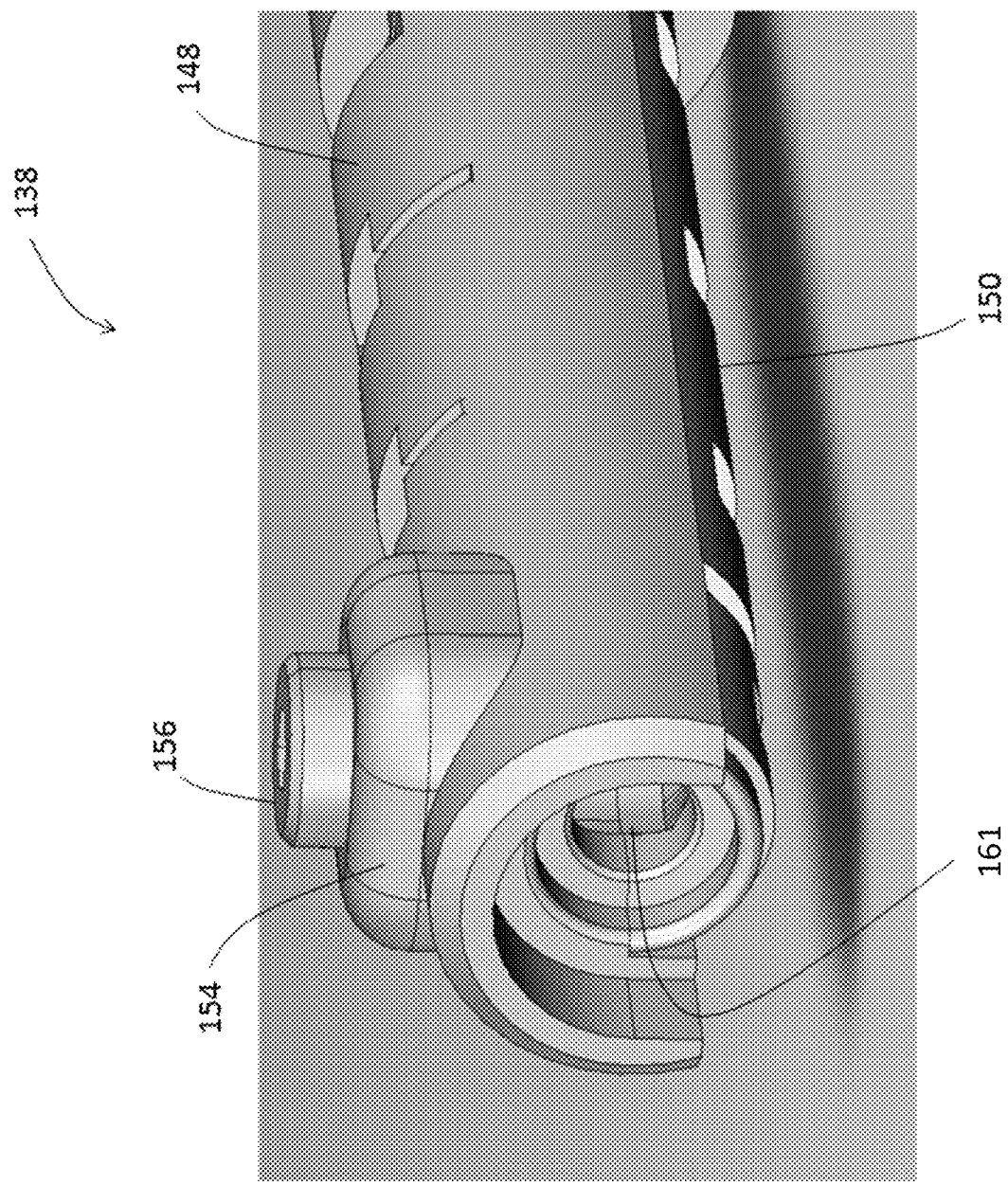

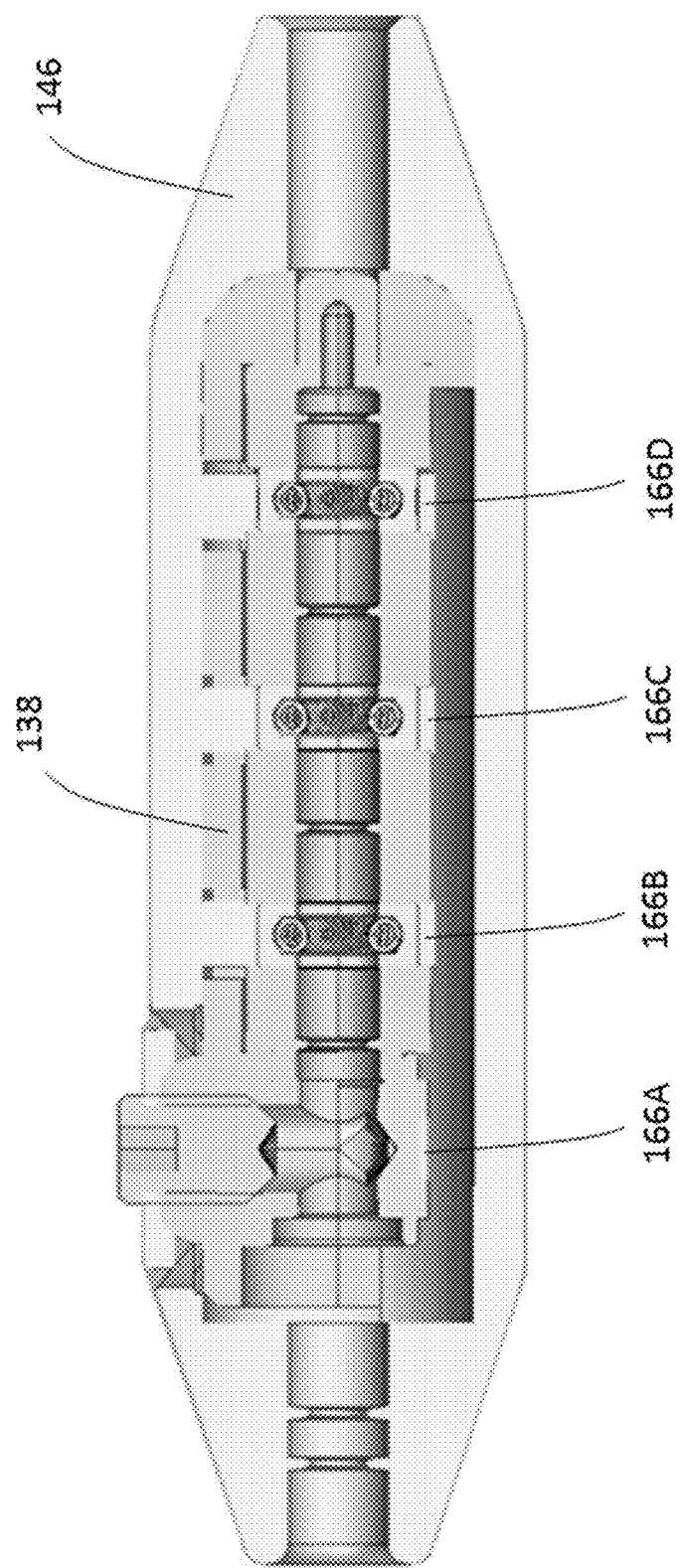

ELECTRICALLY ISOLATED CONNECTOR FOR IMPLANTABLE MEDICAL DEVICES

CROSS-REFERENCE TO RELATED APPLICATIONS

This application claims the benefit of U.S. Application Ser. No. 62/985,026 filed Mar. 4, 2020, which is hereby incorporated herein in its entirety by reference.

FIELD

The present technology is generally related to medical leads for implantable electrical stimulation therapy devices, and more particularly, to electrical connectors that facilitate and electrical coupling between one or more implanted medical leads and circuitry of the implantable electrical stimulation therapy devices.

BACKGROUND

A number of human bodily functions are affected by the nervous system. For example, bodily disorders, such as urinary incontinence, urinary urge/frequency, urinary retention, pelvic pain, bowel dysfunction (constipation, diarrhea, etc.), erectile dysfunction, etc. are all bodily functions influenced by the sacral nerves. One technique to treat such bodily disorders is sacral nerve stimulation therapy. Sacral nerve stimulation therapy is a treatment that uses a small device to send mild electrical impulses to nerves located in the lower region of the spine (just above the tailbone). These nerves, referred to as sacral nerves (specifically S2, S3 and S4), influence the behavior of structures such as the bladder, sphincter and pelvic floor muscles. In some cases, electrical stimulation of the sacral nerves can successfully eliminate or reduce the above mentioned bodily disorders.

Generally, implantation of a sacral neuromodulation system involves surgically implanting a stimulation lead near the sacral nerves. The stimulation lead is a small, insulated, electrical conductor with one or more stimulation electrodes on a distal end for implementation near the sacral nerves, and an electrical connector on the proximal end of the lead. The proximal end electrical connector is typically connected to an implantable neurostimulator device that operates in a fashion broadly similar to that of a cardiac pacemaker by delivering occasional mild electrical pulses to the sacral nerve of the patient.

The power used to generate the mild electrical pulses typically originates from a primary cell or battery located in the implantable neurostimulator device. Over an extended period of use, the battery can become depleted. For example, some currently available implantable neurostimulator devices may have a battery lifetime of about ten years or less. Once the battery is depleted, it is common for patients to have the neurostimulator device removed and replaced.

The emergence of implantable neurostimulator devices with rechargeable batteries has reduced the form factor of such devices. A rechargeable battery may be configured to last only a period of weeks between charges, and thus may be physically smaller in size than a battery intended to last years. As a result of this reduced size, the design of the stimulation leads compatible with newer devices has also changed. In particular, the size or configuration of the electrical connector on the proximal end of the lead has been reduced in size for improved mating with the smaller neurostimulator devices. As a result, some legacy and current stimulation leads may not be compatible with emerging and/or next-generation neuromodulation devices.

Stimulation leads are connectable to implantable medical devices such as neurostimulator devices. A proximal end portion of the lead typically contains a number of connector rings corresponding to the number of electrodes. Conductors run within and along the lead body and electrically couple the connectors to the electrodes. The proximal end portion of the lead is insertable into a lead receptacle of an implantable medical device such that electrical contact is made between discrete contacts in the lead receptacle and the connector rings of the lead. The lead is then typically secured within the lead receptacle of the implantable medical device via a set screw, which provides a compressive force on the lead, for example at one of the connector rings or other suitable structure on the lead. Stimulation leads may also be connectable to lead extensions or lead adapters in a similar fashion.

Certain stimulation leads are configured to be utilized with an active set screw, wherein an electrically conductive set screw provides both a mechanical and an electrical connection between a connector ring of the lead and an implantable medical device, lead extension or lead adapter. With active set screws, care must be taken to prevent inadvertent stimulation of tissue in the vicinity of the set screw. Such "pocket stimulation" is typically prevented by electrically isolating the set screw from tissue of the patient in which the device is implanted. Electrical isolation is often achieved by placing a silicone grommet between the set screw and the outer surface of the device.

By contrast to the neurostimulator device, the stimulation leads typically have a much longer usable lifetime than the neurostimulator device. Further, replacement of the stimulation lead is typically considered a more invasive procedure, as unlike the neurostimulator device which is generally located just beneath the skin of the patient, the stimulation leads can extend much further into the patient and are considered to be more challenging to place correctly. Additionally, many leads include one or more tines or barbs positioned on the distal end of the lead, which serve to anchor the lead in place within the patient as tissue fills in around the lead over time. Accordingly, it is generally considered preferable to leave the stimulation lead in place when the neurostimulator device is replaced. Unfortunately, not all stimulation leads are compatible with all neurostimulator devices. The present disclosure addresses this concern.

SUMMARY

The techniques of this disclosure generally relate to a neuromodulation adaptor configured to enable an electrically compatible connection between otherwise incompatible leads and neurostimulation devices, for example between a previously implanted stimulation lead and a replacement neurostimulator device, so as to increase options when replacing components of a neuromodulation system. A number of factors may cause incompatibility between an implantable stimulation lead and a neurostimulator device, such as variation in the number of electrodes (e.g., one, two, four, etc.) included on the lead, the spacing of electrical contacts on the lead in the region where the lead is connected to the neuro stimulator device, diameter of the lead, and use of active or inactive set screws, for example.

In one aspect, the present disclosure provides a neuromodulation adaptor configured to provide an electrical coupling between an otherwise incompatible stimulation lead and neurostimulator device. The neuromodulation adaptor can include a proximal portion and a distal portion. The proximal portion can include a plurality of electrical conductors spaced apart at a first pitch spacing and configured to electrically engage with a corresponding plurality of electrical terminals of a neurostimulator device. The distal portion can include a stimulation lead port assembly, the stimulation lead port assembly including an upper portion and a lower portion, the upper and lower portions collectively configured to house a plurality of connector elements and a set screw assembly, the plurality of connector elements and set screw assembly spaced apart at a second pitch spacing and configured to electrically engage with a corresponding plurality of electrical connectors of a stimulation lead.

In another aspect, the disclosure provides a set screw assembly including a nonconductive set screw block, a nonconductive set screw and lower contact element. In another aspect, the disclosure provides a set screw assembly further including an o-ring constructed of a non-electrically conductive, deformable polymer, positioned between the set screw and a portion of the set screw block. In another aspect, the disclosure provides a set screw assembly further including one or more protrusions or nubs configured to establish electrical contact between the lower contact element and the plurality of electrical connectors of a stimulation lead. In another aspect, the disclosure provides a set screw assembly further including a spring contact configured to improve electrical contact between the lower contact element and the plurality of electrical connectors of a stimulation lead.

In another aspect, the disclosure provides an upper portion of the stimulation lead port assembly constructed of a nonconductive material. In another aspect, the disclosure provides a nonconductive set screw block of the set screw assembly and an upper portion of the stimulation lead port assembly formed of a single unitary member. In another aspect, the disclosure provides first pitch spacing of at least one of about 0.170 inches, about 0.085 inches, or about 0.080 inches (about 2 mm). In another aspect, the disclosure provides a second pitch spacing of at least one of about 0.170 inches, about 0.085 inches, or about 0.080 inches (about 2 mm).

In another aspect, the disclosure provides a flexible portion located between the proximal portion and the distal portion, configured to enable bending of the neuromodulation adaptor to aid in an ideal positioning of a neurostimulator device relative to a stimulation lead within a body of a patient. In another aspect, the present disclosure provides a plurality of insulated connecting elements coupled with and extending between the conductor elements and the electrical conductors, wherein the plurality of insulated connecting elements are arranged generally linearly through the flexible portion of the neuromodulation adaptor. In another aspect, the present disclosure provides a plurality of insulated connecting elements coupled with and extending between the conductor elements and the electrical conductors, wherein the plurality of insulated connecting elements are arranged in a spiral coil configuration through the flexible portion of the neuromodulation adaptor. In another aspect, the present disclosure provides each of the plurality of insulated connecting elements in the distal portion of the neuromodulation adaptor are routed within channels of the set screw assembly for connection to respective conductor elements. In another aspect, the present disclosure provides each of the plurality of insulated connecting elements are maintained in a spiral coil configuration through the distal portion of the neuromodulation adaptor until generally adjacent a respective conductor element.

In another aspect, the disclosure provides an adaptor configured to provide an electrical coupling between an otherwise incompatible stimulation lead and neurostimulator device, including a stimulation lead port assembly having an upper portion and a lower portion configured to house a plurality of connector elements and a set screw assembly, the plurality of connector elements and set screw assembly spaced apart at a pitch spacing and configured to electrically engage with a corresponding plurality of electrical connectors of a previously implanted stimulation lead.

In another aspect, the disclosure provides a neuromodulation adaptor configured to provide an electrical coupling between an otherwise incompatible stimulation lead and neurostimulator device. The neuromodulation adaptor can include a proximal portion and a distal portion. The proximal portion can include a plurality of electrical conductors spaced apart at a first pitch spacing of at least one of about 0.085 inches or about 0.080 inches (approximately 2 mm) and can be configured to electrically engage with a corresponding plurality of electrical terminals of a neurostimulator device. The distal portion can include a stimulation lead port assembly, including a nonconductive upper portion and a lower portion configured to house a plurality of connector elements and a set screw assembly, the plurality of connector elements and set screw assembly spaced apart at a second pitch spacing of about 0.170 inches and is configured to electrically engage with a corresponding plurality of electrical connectors of a stimulation lead. The set screw assembly can include a nonconductive set screw block, set screw, lower contact element, and o-ring constructed of a non-electrically conductive, deformable polymer, positioned between the set screw and a portion of the set screw block, wherein the set screw assembly further includes one or more nubs configured to improve electrical contact between the lower contact element and the plurality of electrical connectors of a stimulation lead.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 7A is a cross-sectional view depicting a set screw assembly, in accordance with a first embodiment of the disclosure.

FIG. 7B is a cross sectional view depicting a set screw assembly, in accordance with a second embodiment of the disclosure.

FIG. 8 is partial, perspective view depicting a stimulation lead port assembly, in accordance with an embodiment of the disclosure.

FIG. 9 is a cross-sectional view depicting a stimulation lead port assembly coated with a flexible coating, in accordance with an embodiment of the disclosure.

Figure 1:
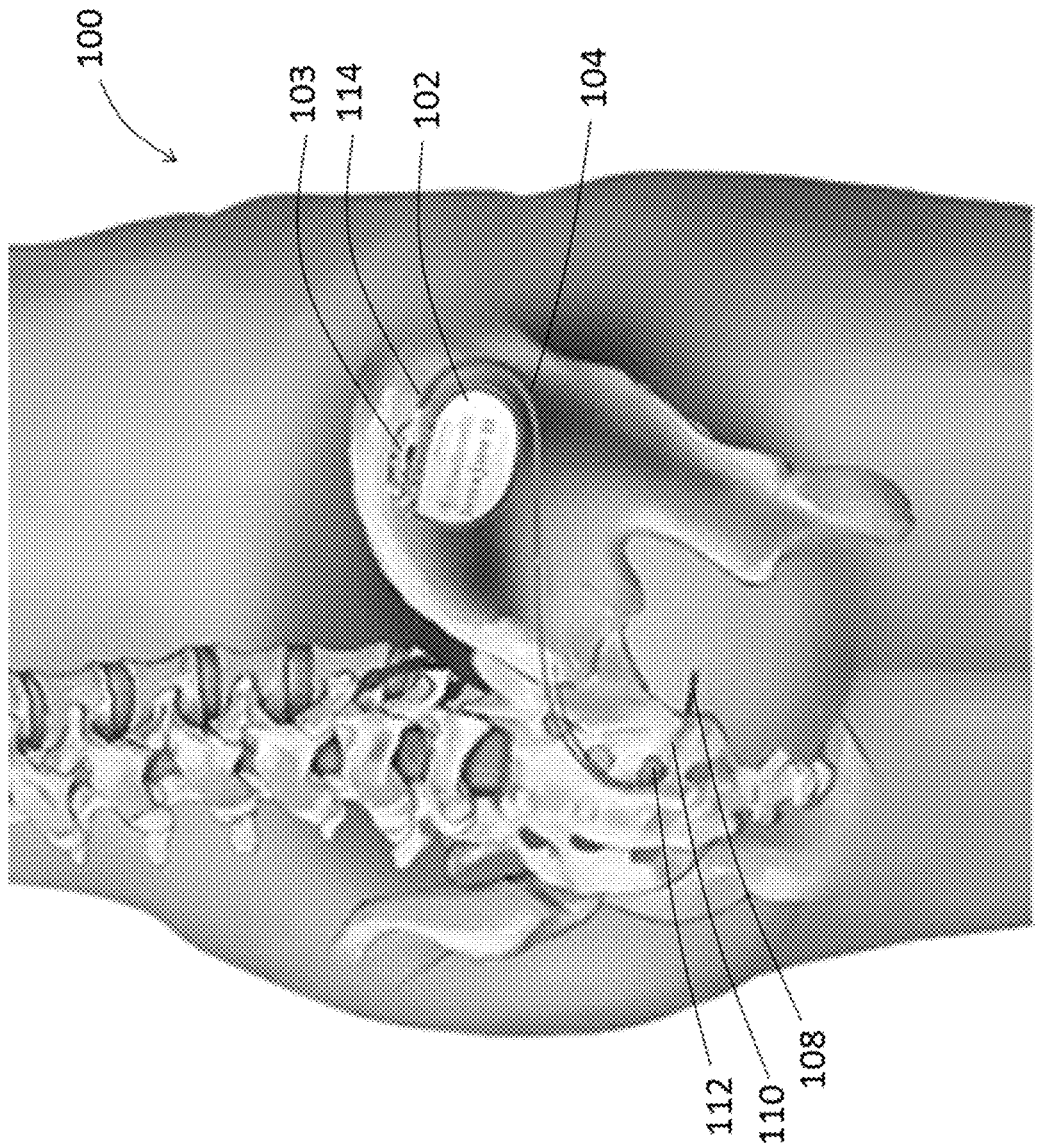
FIG. 1 is a schematic view depicting an implanted neuromodulation system adapted for sacral nerve stimulation, in accordance with the prior art.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

FIG. 1 schematically illustrates an example of an implanted neuromodulation system 100 adapted for sacral nerve stimulation. Neuromodulation system 100 includes an implantable neurostimulator device 102 and an implantable stimulation lead 104 operably coupleable to device 102. Neurostimulator device 102 may be configured to be implanted in a lower buttock region of a patient, and in an embodiment implantable stimulation lead 104 may be configured for stimulation of a sacral nerve. As depicted in FIG. 1, the stimulation lead 104 is oriented through the S3 foramen, although other locations such as S2 or S4 are also contemplated. The stimulation lead 104 can include one or more stimulation electrodes 110 configured to transmit electrical pulses to a nerve, nerve tissue, or other target site within a patient. In an embodiment, electrodes 110 are arranged on a distal portion 108 of lead 104, although other locations are contemplated for electrodes 110. In one embodiment, the stimulation electrodes 110 can be configured as an array of two, three, four or more ring-shaped electrodes for delivering electrical stimulation. In other embodiments, the stimulation lead 104 can include a greater or lesser number of electrodes. The proximal portion 114 of the stimulation lead 104 is configured to be plugged into the neurostimulator device 102, for example via a header 103 of the device 102.

The stimulation lead 104 may be anchored by passive or active fixation, such as a tined anchor portion 112 that maintains a position of a set of stimulation electrodes 110 along or otherwise proximate to a targeted nerve. Over time, tissue surrounding the stimulation lead 104 can grow between the tines 112, thereby aiding in securing the stimulation lead 104 in a fixed position relative to the nerve or other target site within a patient. The stimulation lead 104 can have a variety of shapes, can be a variety of sizes, and can be made of a variety of materials, which size, shape, and materials can be tailored to the specific treatment application. The electrical pulses generated by the neuromodulation system 100 are delivered to one or more targeted sacral nerves via one or more stimulation electrode 110 at or near the distal portion 108 of the stimulation lead 104.

The pulsed electrical stimulation may be to one of several nerves; however, for purposes of describing the system 100, the stimulation site is referred to herein simply as "sacral nerves." It should be understood that the term "sacral nerves" as used herein includes sacral nerves S1, S2, S3, S4, as well as other nerve sites such as the pudendal nerve, superior gluteal nerve, lumbo-sacral trunk, inferior gluteal nerve, common fibular nerve, tibial nerve, posterior femoral cutaneous nerve, sciatic nerve, and obturator nerve. Additionally, stimulation may be provided unilaterally or bilaterally via two leads.

While this embodiment is adapted for sacral nerve stimulation, it is appreciated that similar systems can be used to provide therapy for urinary incontinence, urological disorders and or fecal incontinence. The urological disorders include overflow incontinence, stress incontinence, overactive bladder (OAB), idiopathic chronic urinary retention, interstitial cystitis, neural urological disorder, vescico-urethral dysfunctions, bladder inflammation, bladder pain, pelvic pain, genito-urinary disorders, such as prostatitis, prostatagia, and prostatodynia. Electrical stimulation is typically delivered to the sacral nerve root S3, but may be delivered to the S2, S4 or other sacral nerves or branches such as the pudendal nerves or perineal nerves. In other applications, the stimulation leads 104 may be, for example, implemented in a peripheral portion of a patient's body, such as in the arms or legs, and can be configured to deliver electrical pulses to the peripheral nerve, such as may be used to relieve chronic pain. Stimulation may be applied in bipolar mode, or in unipolar mode where the neurostimulator device 102 is used as an anode. It is appreciated that the stimulation leads 104 and/or the stimulation programs may vary according to the nerves being targeted.

Figure 2:
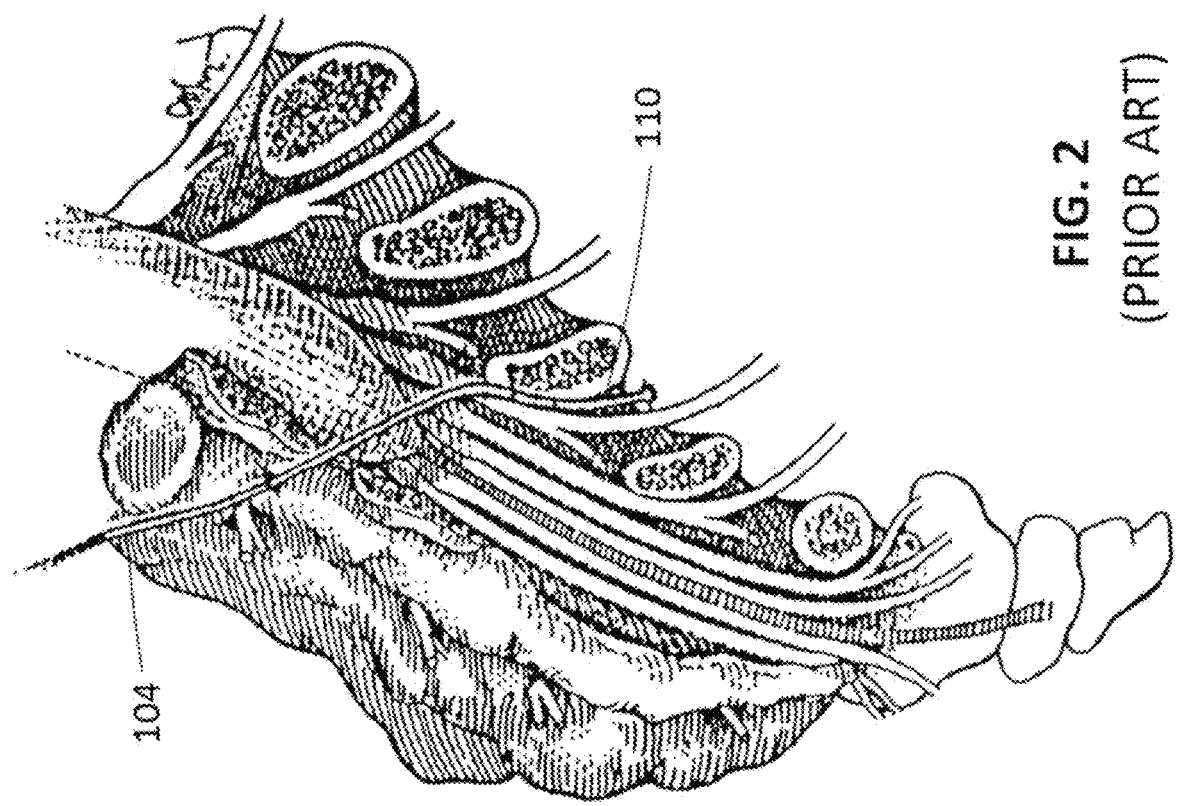
FIG. 2 is a schematic view depicting a stimulation lead implanted near a sacral nerve for stimulation, in accordance with the prior art.

FIG. 2 depicts an overall schematic of the sacral nerve area with the stimulation lead 104 implanted near a sacral nerve for stimulation. The stimulation lead 104 is inserted by first making an incision appropriate to the size of the patient and then splitting the paraspinal muscle fibers to expose the sacral foramen. A physician then locates the desired position and inserts the stimulation lead into the foramen and anchors the stimulation lead 104 in place. The stimulation lead 104 should be placed close enough to the nerve bundles such that the electrical stimulation results in a desired physiological response. The desired physiological response varies depending on which pelvic floor disorder is being treated or which nerve is being stimulated. The preferred position for the implantable lead 104 is implementation in close proximity to the nerve; as such placement results in the most efficient transfer of electrical energy.

To determine the best location of the stimulation lead 104, an insulated needle with both ends exposed for electrical stimulation is often used to locate the foramen and locate the proximity of the nerve by electrically stimulating the needle using an external pulse generator. The location is tested by evaluating the physiological response and by the electrical threshold required to get that response. Once the appropriate location has been determined using the insulated needle, the stimulation lead 104 is implanted in that approximate location. In some embodiments, the stimulation lead 104 is advanced through the foramen until the electrodes 110 are positioned at the anterior sacral nerve root, while the anchoring portion 112 of the lead 104 proximal to the stimulation electrodes 110 are generally positioned dorsal to the sacral foramen through which the lead 104 passes, so as to anchor the lead 104 in position. A proximal portion 114 of the stimulation lead 104 is tunneled subcutaneously to a site where the neurostimulator device 102 is implanted, which is usually in the lower abdominal area (or may be in the gluteal region). The neurostimulator device 102 is connected to the proximal portion 114 of the stimulation lead 104, placed in a subcutaneous pocket, and the tissues are surgically closed in layers. Stimulation therapy can be applied after the tissues are healed from the surgery.

The neurostimulator device 102 may be explanted and replaced if needed, with relative ease. Reasons for replacing neurostimulator device 102 may include battery depletion, malfunctioning of the device, or a desire to upgrade to a newer generation device. In contrast, replacement of a stimulation lead 104 after initial implant is typically undesirable. This is due, in part, because tissue surrounding the stimulation lead 104 typically grows between the tines 112 such that removal of the stimulation lead 104 may cause trauma to the surrounding tissue. Additionally, if a previously implanted stimulation lead 104 was properly positioned to deliver effective therapy to the patient, a surgeon may be reluctant to replace the existing lead, avoiding the need to reevaluate positioning of a replacement lead for a proper physiological response with an insulated needle and external pulse generator, as described above. Accordingly, unless it is determined that the stimulation lead 104 is not functioning properly or is damaged, it may be preferable to reuse a previously implanted stimulation lead 104 should the neurostimulator device 102 require replacement.

Figure 3:
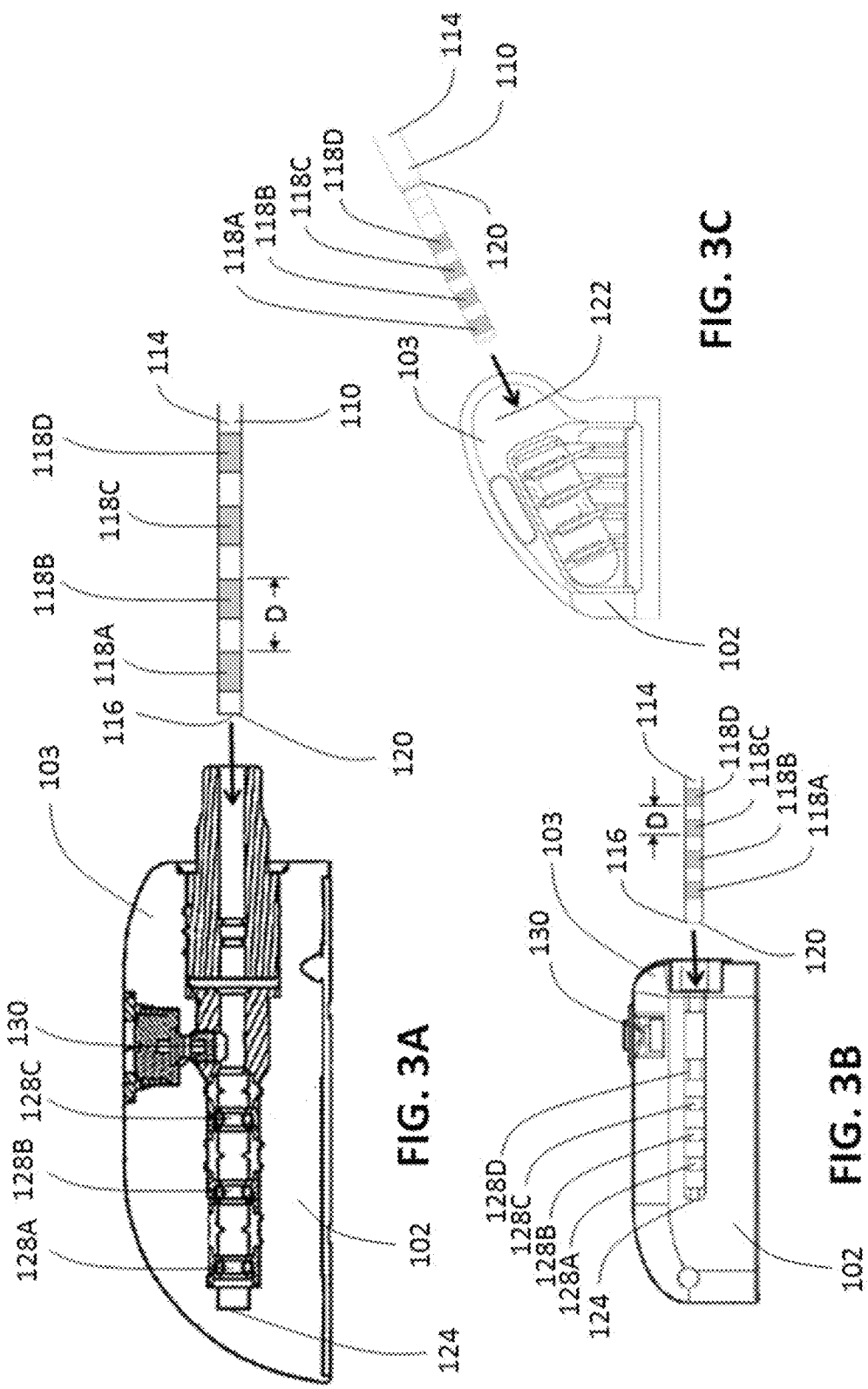
FIG. 3A is a cross-sectional profile view depicting a proximal portion of a stimulation lead and a neurostimulator device, in accordance with a first embodiment of the disclosure.
FIG. 3B is a cross-sectional profile view depicting a proximal portion of a stimulation lead and a neurostimulator device, in accordance with a second embodiment of the disclosure.
FIG. 3C is a cross-sectional profile view depicting a proximal portion of a stimulation lead and a neurostimulator device, in accordance with a third embodiment of the disclosure.

With additional reference to FIGS. 3A-C, the proximal portion 114 of the stimulation lead 104 can include one or more electrical connectors 118 configured to be operably coupled to the header 103 of a neurostimulator device 102 or coupling device 106 (referred to herein as an "adapter" or "adaptor"). As depicted, the proximal portion 114 can include an array of four insulated ring-shaped connectors; although a greater or lesser number of connectors is also contemplated.

As depicted, the connectors 118 can be separated or spaced apart from one another at a fixed distance D, alternatively referred to as "pitch spacing" or "pitch." For example, in one embodiment, the plurality of connectors 118A-D can be spaced apart from one another at a pitch of approximately 0.170 inches (as depicted in FIG. 3A). In another embodiment, the plurality of connectors 118A-D can be spaced apart from one another at a pitch of approximately 0.085 inches (as depicted in FIG. 3B). In yet another embodiment, the plurality of connectors 118A-D can be spaced apart from one another at a pitch of approximately 2 mm (as depicted in FIG. 3C). Other pitch spacing configurations are also contemplated. In addition to varying pitch spacing configurations, different stimulation leads 104 can differ in their outer diameter dimensions, general shape (e.g., blunt, tapered or rounded proximal end 115), as well as other physical characteristics.

In some embodiments, the proximal portion 114 can include a datum reference 120 configured to serve as a reference point for the spacing of the various connectors 118 or configured to serve as a physical stop when inserting the lead into a neurostimulator. For example, in one embodiment, the datum reference 120 can be located on the proximal end 116 of the stimulation electrode 110 (as depicted in FIGS. 3A and 3B), such that insertion of the lead 104 into the neurostimulator device until the datum reference 120 (e.g., proximal end 116) contacts a forward stop 124 thereby aligns the connections 118A-D of lead 104 with the corresponding connector elements 128A-D of a header 103 of the neurostimulator device 102 and/or adapter 106. In another embodiment, the datum reference 120 can be located distally from the connectors 118A-D (as depicted in FIG. 3C), such that insertion of the lead 104 into the header 103 until the datum reference 120 contacts an abutting surface 122 thereby aligns the connectors 118A-D of lead 104 with the corresponding connector elements 128A-D of the header 103 and/or adapter 106.

In some embodiments, the neurostimulator device 102 and/or adapter 106 can include a set screw 130 configured to tighten against the proximal portion 114, thereby enabling the proximal portion 114 of the stimulation lead 104 to be secured in position relative to the neurostimulator device 102 and/or adapter 106. In some embodiments, the set screw 130 can be configured to contact at least one of the connectors 118D (as depicted in FIG. 3A), so as to be electrically active. In other embodiments, (as depicted in FIG. 3C) the set screw 130 can be electrically inactive, in that it does not contact any of the connectors 118A-D but may rather contact another portion of the stimulation lead, such as the datum reference 120 or an inactive clamping portion. In embodiments, adapter 106 may include a plurality of set screws, which may allow adapter 106 to be utilized with multiple diameters of stimulation leads 104.

Figure 4:
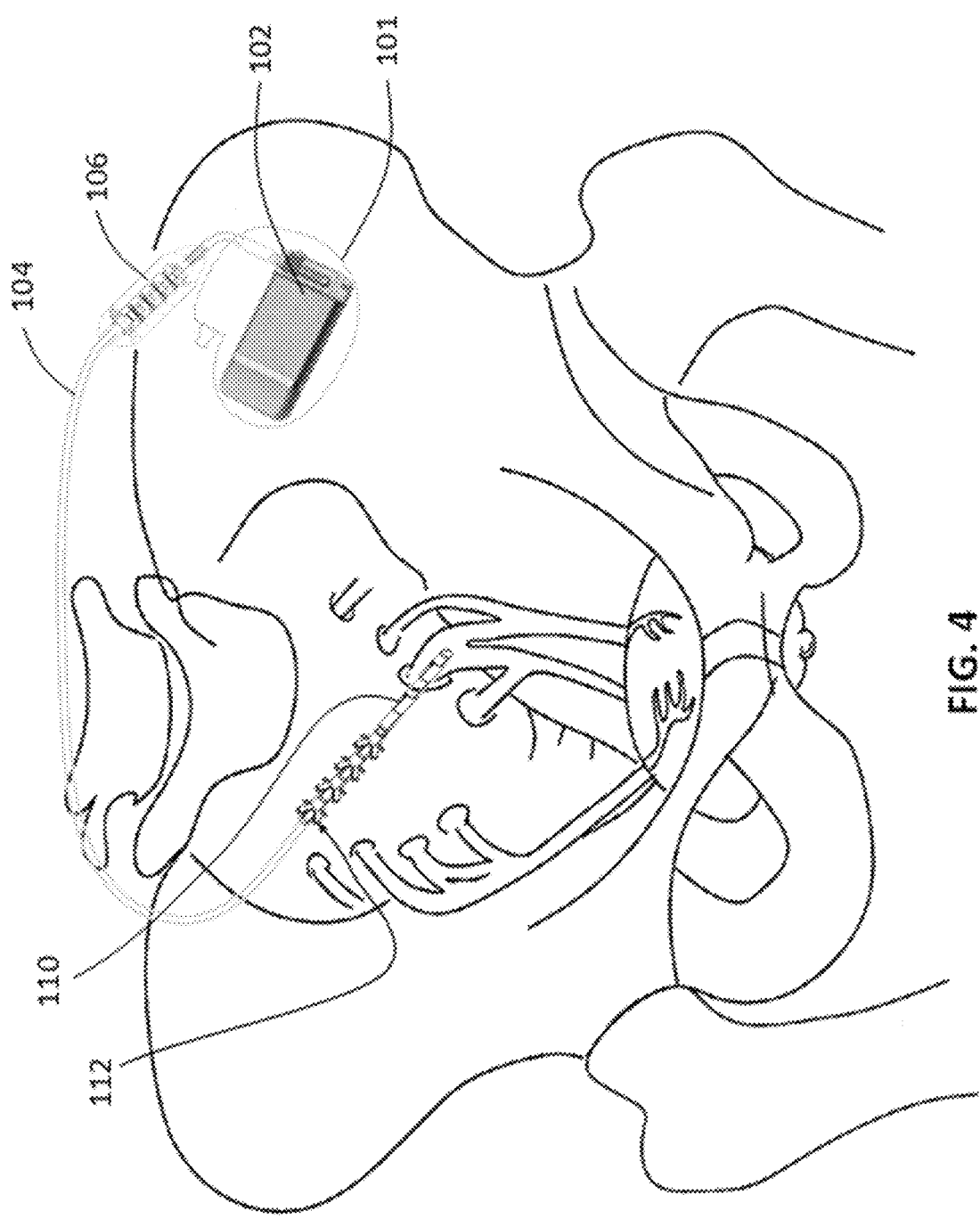
FIG. 4 is an assembly view depicting an adapted neuromodulation system, including a replacement neurostimulator device, previously implanted stimulation lead, and adaptor electrically coupling the otherwise incompatible stimulation lead and replacement neurostimulator device, in accordance with a first embodiment of the disclosure.

With reference to FIG. 4, in some cases it may be desirable to replace a previously implanted neurostimulator device 101 with a replacement device 102, particularly where the previously implanted device has reached or is nearing the end of its serviceable life (e.g., the previously implanted neurostimulator device may have a primary cell or battery that is near exhaustion), or is otherwise not functioning as desired. In such cases, the replacement device 102 may be more compact and/or have a different shape than the previously implanted device. For example, FIG. 4 depicts an outline shaped similarly to an Interstim II sacral neuromodulation neurostimulator device 101 (manufactured and sold by Medtronic, Inc.), into which a replacement neurostimulator device 102 can be positioned. Accordingly, a replacement neurostimulator device 102 can differ both in shape and size from the previously implanted device 101. For example, the previously implanted device 101 can be a "large neuromodulation device," having a volume of about 10 cc's or more (e.g. the Interstim II device, having a volume of about 14 cc), while the replacement neurostimulator device 102 can be a "small neuromodulation device," having a volume of about 10 cc or less or about 5 cc or less (e.g., the Axonics r-SNM from Axonics Modulation Technologies having a volume of about 5 cc, or the Medtronic Interstim Micro device, having a volume of about 3.5 cc). Alternatively, the previously implanted device 101 can be a small neuromodulation device, and the replacement neurostimulator device 102 can be a large neuromodulation device. The stated volumes of such devices generally refer to the implantable medical device only (e.g., device 101 or device 102), and do not include the volume of any associated leads or adapters which may be coupled to such devices.

Other differences may include the orientation or angle at which the stimulation lead extend from the devices 101, 102, as well as the connector 118 pitch spacing of the stimulation leads designed to be used with the different devices 101, 102. For example, a previously implanted stimulation lead may have an electrical connector with a pitch spacing of about 0.170 inches, while the replacement neurostimulator device 102 may be configured to receive a stimulation lead having connectors 118 with a pitch spacing of about 0.085 inches or about 2 mm (about 0.080 inches). Accordingly, without modification, such as an adapter 106, a replacement device 102 may be incompatible with a previously implanted stimulation lead 104.

Figure 5:
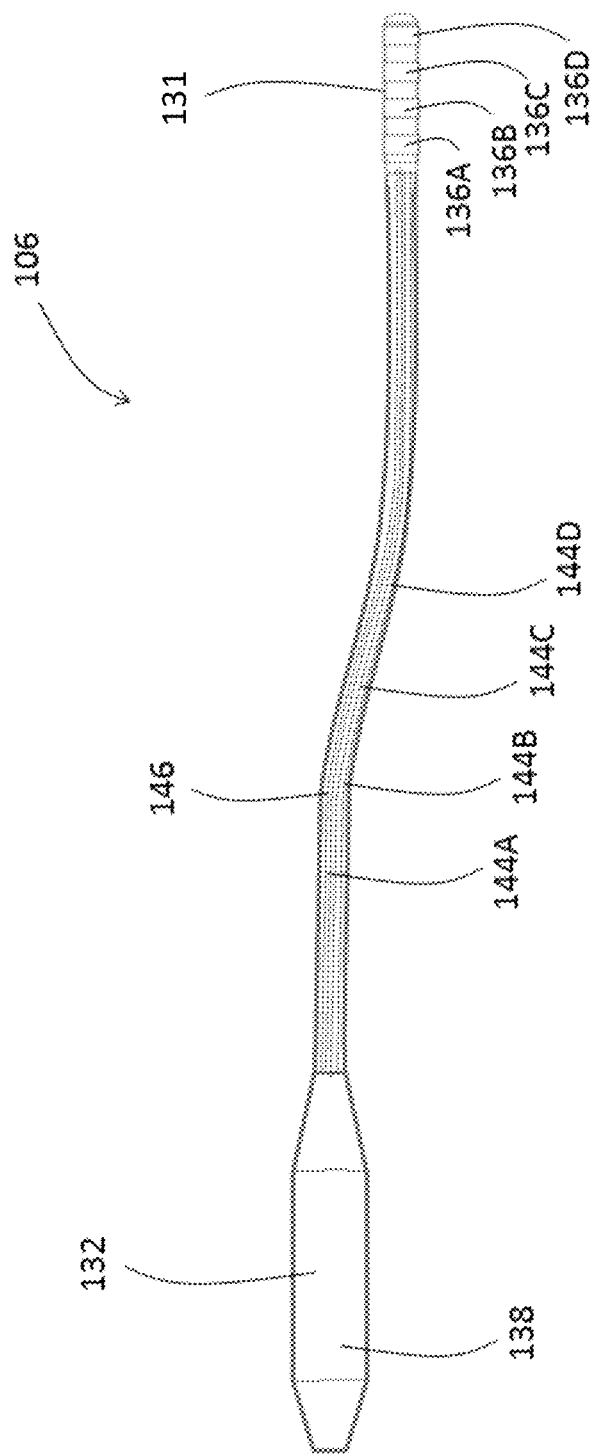
FIG. 5 is a side elevation view depicting a stimulation lead port assembly, in accordance with an embodiment of the disclosure.

With reference to FIG. 5, in one embodiment, the adapter 106 can include a proximal portion 131 and a distal portion 132. The proximal portion 131 can be configured to be received within a stimulation lead port of a neurostimulator device. For example, in some embodiments, the proximal portion 131 of the adapter 106 can be configured to be received within a header 103 of the neurostimulator device 102 (as depicted in FIGS. 3A-C). The proximal portion 132 can include one or more electrical conductors 136A-D. For example, in one embodiment, the adapter 106 can include four electrical conductors 136A-D configured to electrically couple to the corresponding connector elements 128 of a neurostimulator device 102.

Figure 6B:
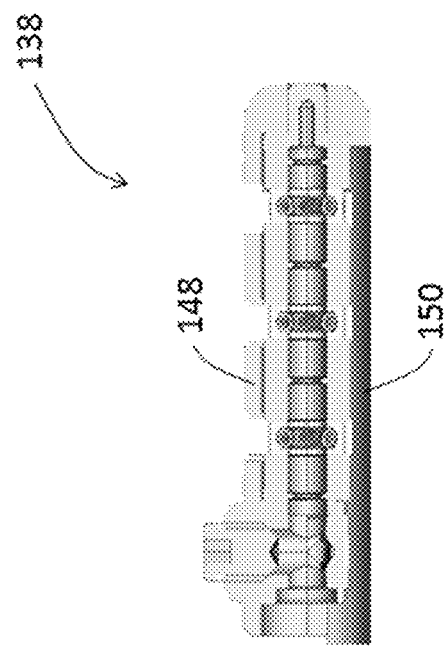
FIG. 6B is a cross-sectional view depicting the assembled stimulation lead port assembly of FIG. 6A.
Figure 6A:
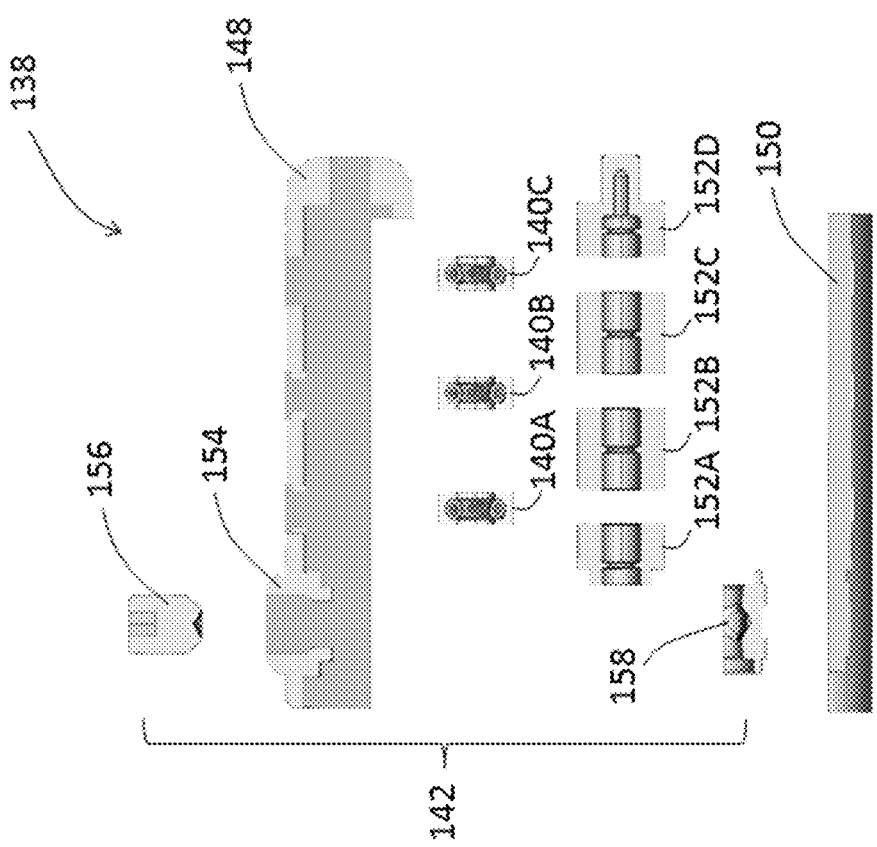
FIG. 6A is an exploded, cross-sectional view depicting a stimulation lead port assembly, in accordance with an embodiment of the disclosure.

The distal portion 132 of the adapter 106 can be configured to receive a proximal portion 114 of a stimulation lead 104. For example, in one embodiment, the distal portion 132 can include a stimulation lead port assembly 138, including one or more connector elements 140A-C and set screw assembly 142 (as depicted in FIGS. 6A-B) electrically coupling the connectors 118 of the stimulation lead 104 to the adapter 106. Stimulation lead port assembly 104 may alternately be referred to as a lead housing or a lead connector housing.

A plurality of conductors such as wires, cables or other connecting elements 144A-D traversing along a length of the adapter 106 can operably couple the connector elements 140 and set screw assembly 142 on the distal portion 132 of the adapter 106 to the electrical conductors 136A-D on the proximal portion 131 of the adapter 106. Connecting elements 144A-D can take a variety of constructions or configurations, as described in more detail below. In some embodiments, a portion of the adapter 106 between the proximal portion 131 and the distal portion 132 can be flexible, so as to enable bending of the adapter 106 to aid in an ideal positioning of the neurostimulator device 102 relative to the stimulation lead 104 within the body of a patient.

In some embodiments, the adapter 106 can further include a flexible coating 146, which can serve to retain components of the adapter 106 in a fixed position relative to one another as well as to isolate the components from bodily fluids. For example, in one embodiment, the flexible coating 146 can be a biocompatible over-molded silicone rubber, or similar such material. In other embodiments, flexible coating 146 could be over-extruded, or extruded separately and placed installed over the adapter.

FIGS. 6A-B show a stimulation lead port assembly 138 prior to a flexible coating 146 being applied. In general, the stimulation lead port assembly includes an upper portion 148 and a lower portion 150, which can be fit together to contain the connector elements 140A-C, set screw assembly 142, and insulative spacers 152A-D. In one embodiment, the connector elements 140A-C can form complete circular structures, examples of which include Bal Seal® canted coil connectors. The connector elements 140A-C can be separated from one another by insulative spacers 152A-D, such that the connector elements 140A-C and insulative spacers 152A-D are interleaved along a longitudinal axis of the stimulation lead port assembly 138. The insulative seals 152A-D can provide wiper seals and can be constructed of a biocompatible compliant material such as silicone. In some embodiments, the insulative seals 152A-D can be compressible to some degree along the longitudinal axis, to create a tight fit between adjacent connector elements 140A-C. In embodiments, insulative spacers 152A-D may be formed as part of flexible coating 146.

The set screw assembly 142 can include a set screw block 154, set screw 156, and lower contact element 158. In one embodiment, the set screw block 156, which can be integrally molded into the upper portion 148, can be configured to enable threaded insertion of the set screw 156 into the set screw block 154. In some embodiments, the upper portion 148 can be constructed of a non-electrically conductive material. In some embodiments, the set screw 156 can also be constructed of a non-electrically conductive material. Examples of non-electrically conductive materials include polymers, such as polyether ether ketone (PEEK), among other suitable materials.

The contact element 158 can be configured to establish electrical communication between a connector 118 of the implanted stimulation lead 104 and an electrical conductor 136 of the adapter 106. In some embodiments, the contact element 158 can be integrally molded within the lower portion 150, such that the entire lower portion 150 is electrically active. In other embodiments, lower portion 150 and contact element 158 can be distinct components, and the lower portion can be constructed of a non-electrically conductive material. FIG. 6B depicts an assembled stimulation lead port assembly 138 without a flexible coating 146.

With reference to FIG. 7A, in one embodiment, electrical communication between the implanted stimulation lead 104 and the contact element 158 can be enhanced by the presence of one or more nubs 160A-C, which can extend outwardly from the contact element 158 towards a connector 118 of the stimulation lead 104. In some embodiments, the nubs 160A-C can have a blunt or rounded surface configured to deform slightly in the presence of a stimulation lead 104, thereby enabling improved surface contact between the contact element 158 and the connector 118 of the stimulation lead 104. Although FIG. 7A depicts three nubs 160A-C, a greater or lesser quantity of nubs 160 is also contemplated.

Alternatively, with reference to FIG. 7B, in another embodiment, electrical communication between the implanted stimulation lead 104 and the set screw block 154 can be enhanced by the presence of a spring contact 162 positioned between the contact element 158 and a connector 118 of the stimulation lead 104. In some embodiments, the spring contact 162 can be configured to deform slightly in the presence of a stimulation lead 104, thereby enabling improved surface contact between the contact element 158 and the connector 118 of the stimulation lead.

With continued reference to FIGS. 7A-B, in some embodiments an optional o-ring 164 constructed of a non-electrically conductive, deformable polymer, such as silicone rubber can be positioned between the set screw 156 and a portion of the set screw block 154 to create a fluid and electrical isolation barrier between contact element 158 and bodily fluids exterior to the stimulation lead port assembly 138. In some embodiments, the o-ring 164 can optionally be formed as a part of the flexible coating 146.

With reference to FIG. 8 a perspective view of the assembled stimulation lead port assembly 138 prior to the application of a flexible coating 146 is depicted. The upper portion 148 and lower portion 150 are designed such that, when assembled, the two portions 148/150 define an aperture 161 shaped and sized to enable the insertion of the proximal portion 114 of an implanted stimulation lead 104 therein. As depicted, the set screw block 154 can be integrated with the upper portion 148 to form a single unitary member and can be constructed of a non-electrically conductive material. The set screw 156, which can be credibly received within the set screw block 154, can be constructed of a similar material.

With reference to FIG. 9, upon assembly of the stimulation lead port assembly 138, the plurality of wires, cables or other connecting elements 144A-D can be operably coupled to the respective contact element 158 and connector elements 140A-C. In some embodiments, the lower portion 150 can define one or more channels 166A-D configured to expose the underside of the contact element 158 and connector elements 140A-C as well as to provide a space in which to route the connecting elements 144A-D, thereby enabling the connecting elements 144A-D to be electrically coupled to the contact element 158 and connector elements 140A-C via a bond, such as one of various types of welds including a resistance spot weld. The opposite end of the connecting elements 144A-D can be operably coupled to the electrical conductors 136A-D on the proximal portion 131 of the adapter 106. The entire assembly can then be coated with the flexible coating 146. Further, in some embodiments, the adapter 106 can be magnetic resonance imaging (MRI) compatible.

Forming the upper portion 148 (including the set screw block 154) and set screw 156 of a non-electrically conductive material, enables the production of a smaller adapter 106. In particular, the use of a non-electrically conductive material for upper portions of the adapter 106 enables the elimination of a grommet, which is traditionally used on neurostimulator devices 102 to electrically isolate an active set screw from the patient.

Figure 10A:
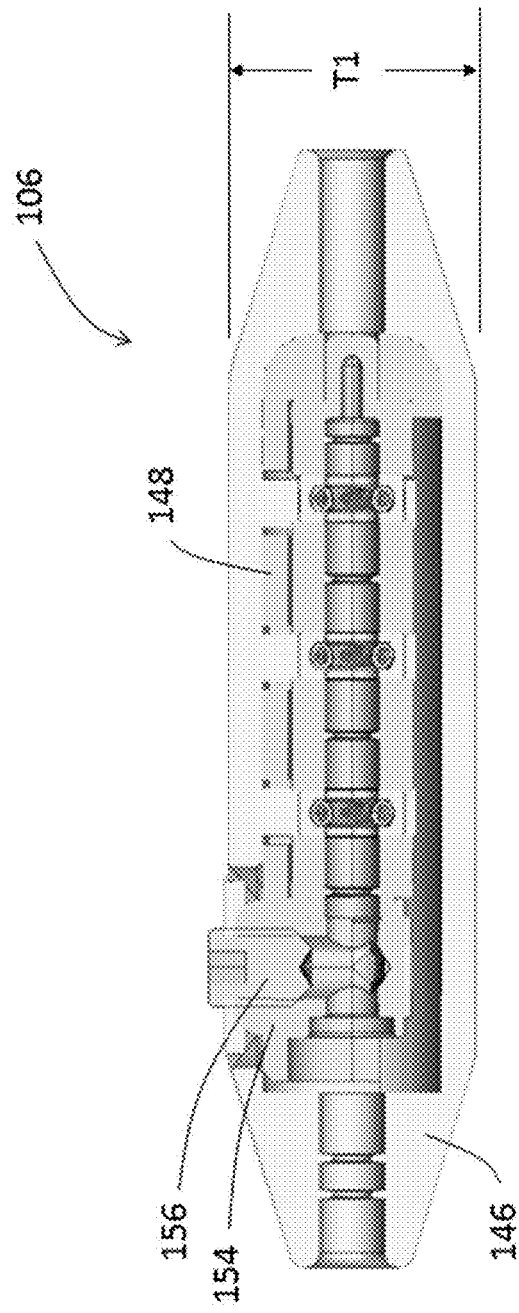
FIG. 10A is a cross-sectional view depicting a stimulation lead port assembly having a non-electrically active upper portion, in accordance with an embodiment of the disclosure.
Figure 10B:
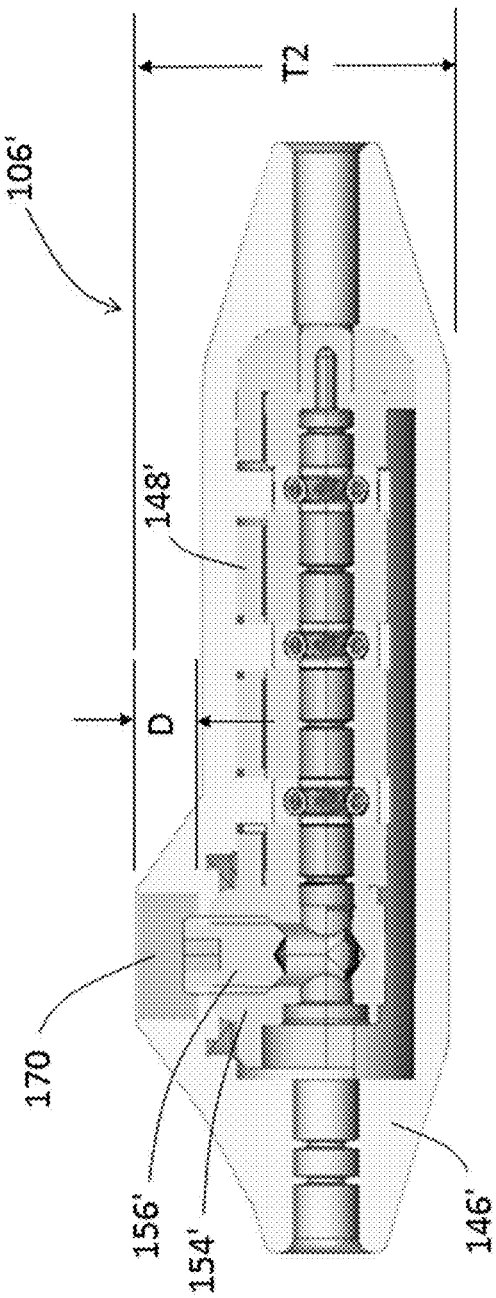
FIG. 10B is a cross-sectional view depicting a stimulation lead port assembly having an electrically active upper portion, including an electrically isolating grommet, in accordance with an embodiment of the disclosure.

FIGS. 10A-B offer a comparison between an adapter 106 having a non-electrically conductive set screw 156, and an alternative adapter 106' having an electrically active set screw 156'. As depicted in FIG. 10B, the alternative adapter 106' includes a grommet or septum 170 configured to electrically isolate the electrically active set screw 156' from the patient (e.g., tissue, bodily fluid, etc.) to inhibit a bleed through of electrical energy into the body of the patient in proximity to the set screw 156'. Where a grommet 170 is utilized, the flexible coating 146' surrounding other components of the adapter 106' is typically built up around the grommet 170, thereby enabling a fluid resistant seal around the grommet 170 for electrical isolation of the electrically active components. Grommet 170 may be pierceable or otherwise configured to allow passage of a tool therethrough, while maintaining electrical isolation and preventing fluid ingress.

As can be seen in a comparison of the two adapters 106, 106', elimination of the grommet 170 enables a reduction in the overall size of the adapter 106. In particular, elimination of the grommet 170 enables the diameter or thickness of the adapter 106 to be reduced by the thickness (D) of the grommet, which in some cases can be approximately one third of the diameter or thickness (T2) of the adapter 106'. Accordingly, in some embodiments, forming the upper portion 148 (including the set screw block 154) and set screw 156 of a non-electrically conductive material, enables the construction of a smaller, more compact adapter 106, having a reduced diameter or thickness (T1). Moreover, in cases where the grommet 170 is unable to maintain a fluid tight seal (particularly over the course of several years in which the adapter 106' may be implanted), adapters 106 having a non-electrically conductive upper portion exhibit improvements in energy efficiency, as they are less likely to exhibit a loss of electrical energy into the patient in proximity to the set screw 156.

Accordingly, in some embodiments, the adapter 106 can be configured to establish a compatible electrical connection between a neurostimulator device 102 (which may be a replacement for a previously implanted neurostimulator device) and an implantable stimulation lead 104 (which may have been previously implanted into the patient). For example, in one embodiment, the neuromodulation adapter 106 can be configured to electrically connect a previously implanted stimulation lead 104 having a plurality of electrical connectors 118 spaced apart from one another at a first pitch with a replacement neurostimulator device 102 generally configured to mate with a stimulation lead 104 having a plurality of electrical connectors 118 spaced apart from one another at a second pitch.

In one embodiment, the first pitch can be approximately 0.170 inches, and the second pitch can be approximately 0.085 inches. Alternatively, the first pitch can be approximately 0.085 inches, and the second pitch can be approximately 0.170 inches. In another embodiment, the first pitch can be approximately 0.170 inches, and the second pitch can be approximately 0.080 inches (approximately 2 mm). Alternatively, the first pitch can be approximately 0.080 inches (approximately 2 mm), and the second pitch can be approximately 0.170 inches. In yet another embodiment, the first pitch can be approximately 0.085 inches, and the second pitch can be approximately 0.080 inches (approximately 2 mm). Alternatively, the first pitch can be approximately 0.080 inches (approximately 2 mm), and the second pitch can be approximately 0.085 inches.

Figure 11:
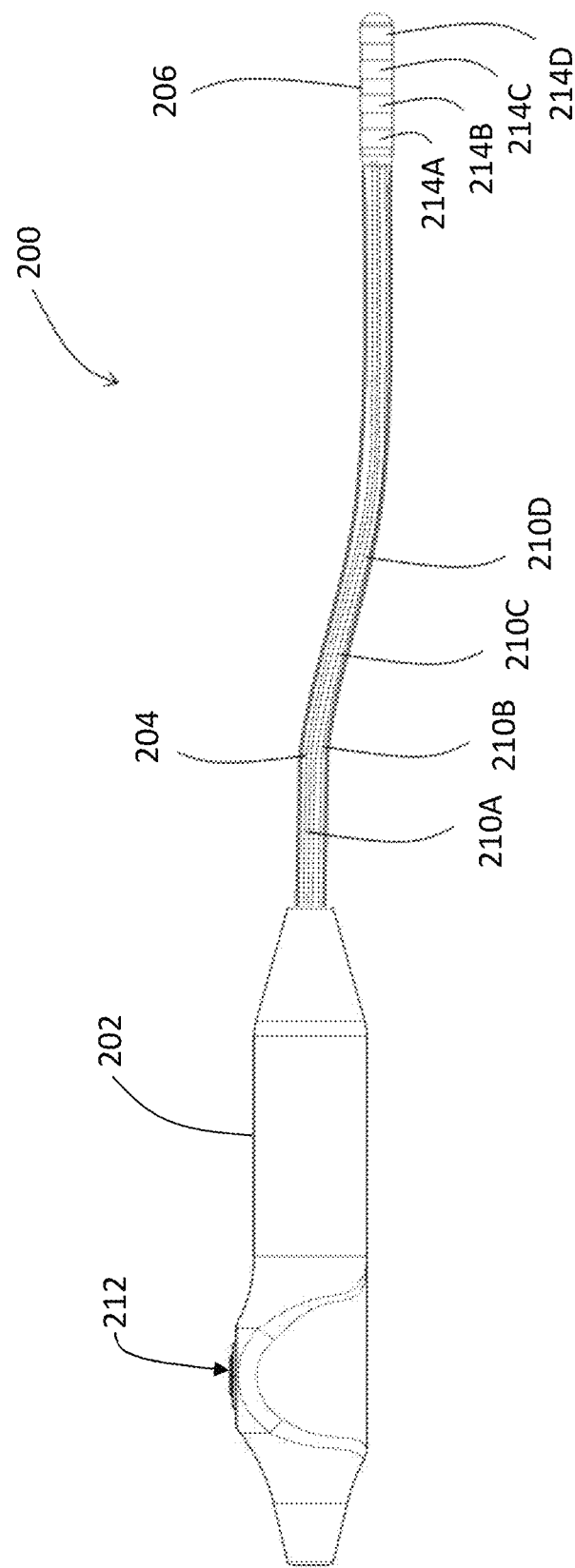
FIG. 11 is a side elevation view depicting a cable adapter, in accordance with an embodiment of the disclosure.

Referring now to internal constructions and configurations of coupling devices (or adapters), FIG. 11 depicts a cable adapter 200 according to an embodiment. Cable adapter 200 generally includes a distal portion 202, middle portion 204 and a proximal portion 206. The distal portion 202 can be configured to receive and couple with a proximal portion of a stimulation lead, and the proximal portion 206 can be configured to be received within a stimulation lead port of a neurostimulator device. The middle portion 204 extends between the distal portion 202 and the proximal portion 206, and houses a plurality of wires, cables or other connecting elements 210A-D.

In an embodiment, connecting elements 210A-D may comprise generally linear lengths of wire that traverse generally parallel to each other along middle portion 204 to operably couple connector elements within a set screw assembly 212 of the distal portion 202 to electrical conductors 214A-D within the proximal portion 204. Connecting elements 210A-D can be secured to connector elements within the set screw assembly and to electrical conductors 214A-D by, for example, resistance spot welding. Each connecting element 210A-D can be individually insulated, such as with ETFE (ethylene tetrafluoroethylene) or other suitable materials. The middle portion 204 of cable adapter 200 can be flexible, so as to enable bending of the cable adapter 200 to aid in an ideal positioning of the neurostimulator device relative to the stimulation lead within the body of a patient. In some embodiments, the cable adapter 200 can further include a flexible outer coating, which can serve to retain components of the cable adapter 200 in a fixed position relative to one another as well as to isolate the components from bodily fluids. For example, in one embodiment, the flexible coating can be a biocompatible over-molded silicone rubber, or similar such material.

Referring now to FIGS. 12A-13B, an adapter 300 is depicted according to an embodiment. Adapter 300 generally includes a distal portion 302, a middle portion 304, and a proximal portion 306. The distal portion 302 can be configured to receive and couple with a proximal portion of a stimulation lead, and the proximal portion 306 can be configured to be received within a stimulation lead port of a neuro stimulator device. The middle portion 304 extends between the distal portion 302 and the proximal portion 306 and houses a plurality of wires, cables or other connecting elements 310A-D.

Figure 12A:
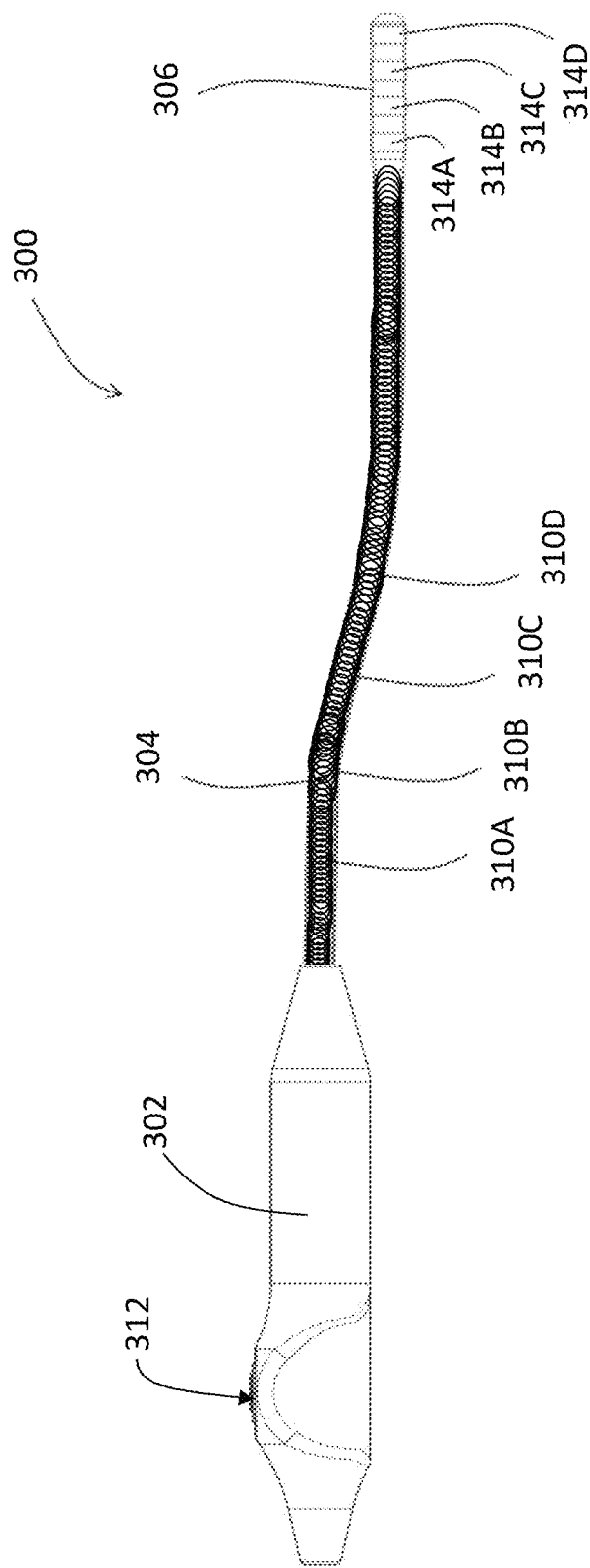
FIG. 12A is a side elevation view depicting an adapter, in accordance with an embodiment of the disclosure.
Figure 12B:
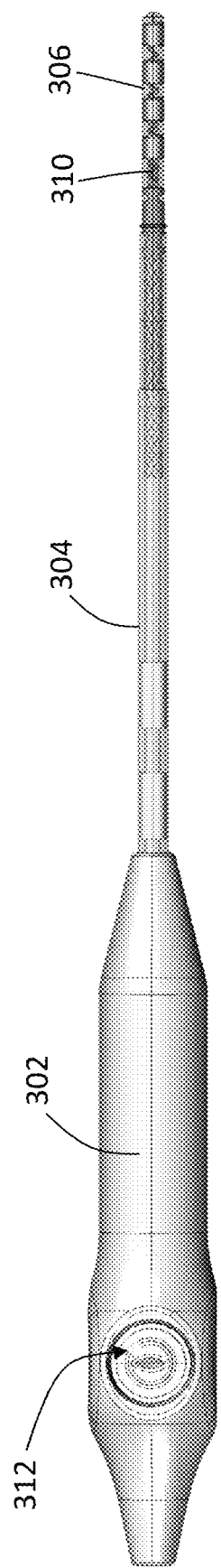
FIG. 12B is a top plan view of the adapter of FIG. 12A.
Figure 12C:
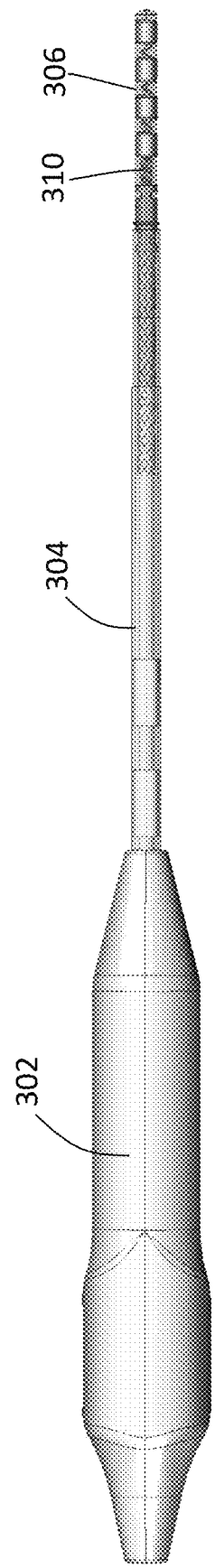
FIG. 12C is a bottom plan view of the adapter of FIG. 12A.

As best depicted schematically in FIG. 12A, connecting elements 310A-D are arranged in a spiral coil configuration along middle portion 304 and in proximal portion 306, to operably couple connector elements 316 within a set screw assembly 312 of the distal portion 302 to electrical conductors 314A-D within the proximal portion 304. Connecting elements 310A-D can be secured to connector elements within the set screw assembly and to electrical conductors 314A-D by, for example, resistance spot welding. Each connecting element 310A-D can be individually insulated, such as with ETFE or other suitable materials. Arranging the connecting elements 310A-D in a spiral coil configuration along middle portion 304 provides flexibility and reduces potential for strain or fatigue of connecting elements 310A-D during bending or twisting of middle portion 304.

Figure 13A:
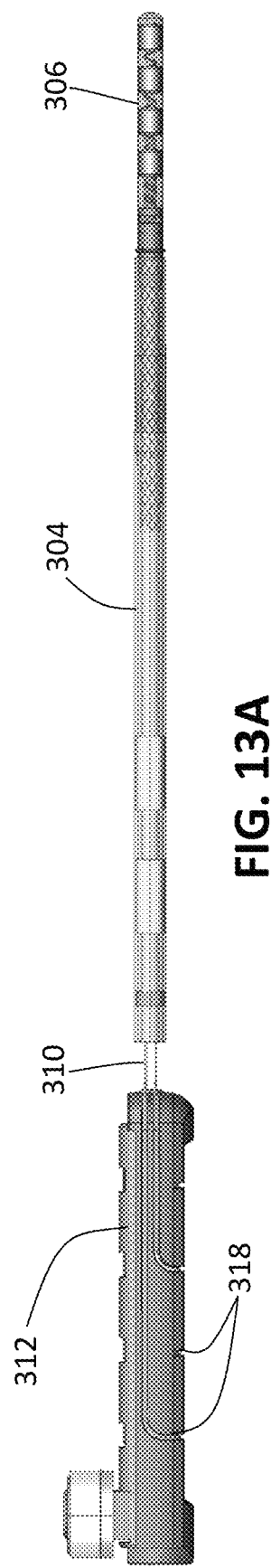
FIG. 13A is a side elevation view of the adapter of FIG. 12A, without a flexible coating over the stimulation lead port assembly.
Figure 13B:
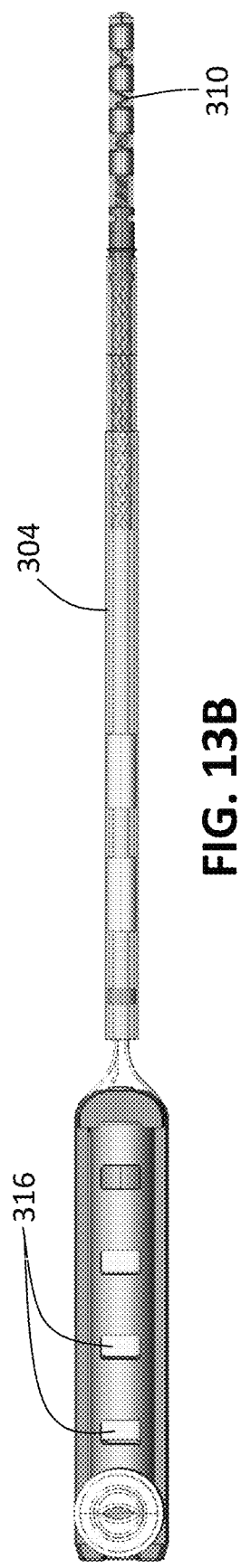
FIG. 13B is a top plan view of the adapter of FIG. 12A without a flexible coating over the stimulation lead port assembly.

As best depicted in FIG. 13A, connecting elements 310A-D of adapter 300 can be configured to include uncoiled segments generally in the distal portion 302 that can be routed through channels 318 within set screw assembly 312, so as to operably couple connecting elements 310A-D with respective connector elements 316.

The middle portion 304 of adapter 300 can be flexible, so as to enable bending of adapter 300 to aid in an ideal positioning of the neurostimulator device relative to the stimulation lead within the body of a patient. In some embodiments, adapter 300 can further include a flexible coating, which can serve to retain components of adapter 300 in a fixed position relative to one another as well as to isolate the components from bodily fluids. For example, in one embodiment, the flexible coating can be a biocompatible over-molded silicone rubber, or similar such material.

Figure 15:
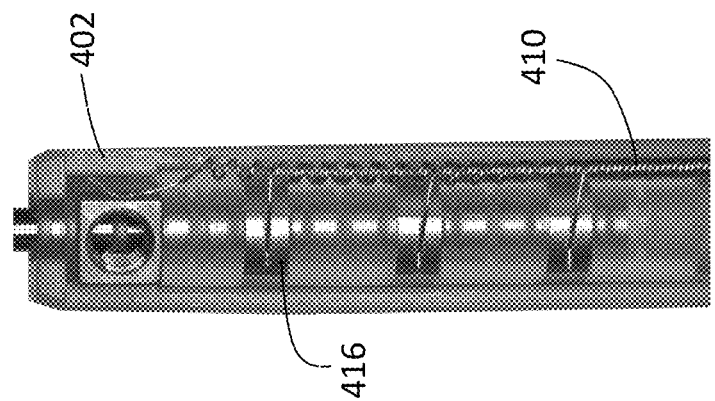
FIG. 15 is a partial, cross-sectional plan view of a coil adapter, in accordance with an embodiment of the disclosure.
Figure 14:
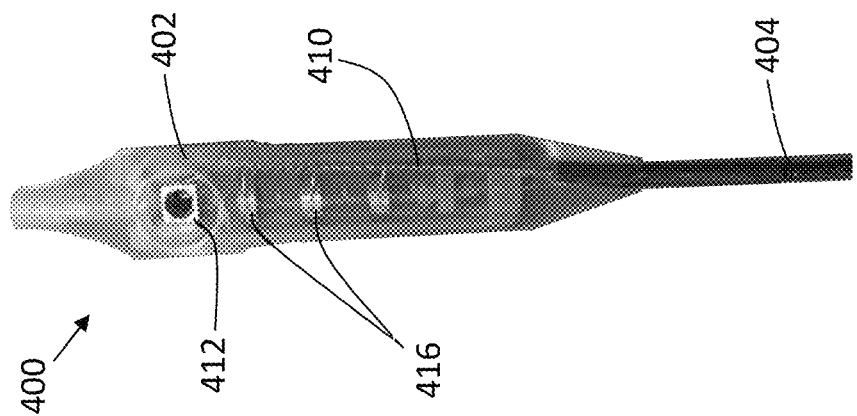
FIG. 14 is a partial plan view of a coil adapter, in accordance with an embodiment of the disclosure.

Referring now to FIGS. 14 and 15, a coil adapter 400 is depicted according to an embodiment. Coil adapter 400 generally includes a distal portion 402, a middle portion 404, and a proximal portion (not pictured). The distal portion 402 can be configured to receive and couple with a proximal portion of a stimulation lead. The proximal portion of coil adapter 400 can be configured to be received within a stimulation lead port of a neurostimulator device. The middle portion 404 extends between the distal portion 402 and the proximal portion and houses a plurality of wires, cables or other connecting elements 410.

Each of the plurality of connecting elements 410 are configured to operably couple connector elements 416 within a set screw assembly 412 of the distal portion 402 to electrical conductors within the proximal portion. As depicted in FIGS. 14 and 15, the plurality of connecting elements 410 are arranged in a spiral coil configuration along substantially all of the distance between connector elements 416 within the distal portion 402 and the electrical conductors within the proximal portion of adapter 400. In contrast to adapter 300, in distal portion 402 of adapter 400 each of the plurality of connecting elements 410 are maintained in a spiral coil configuration until generally adjacent a respective connector element 416.

Each of the plurality of connecting elements 410 can be secured to connector elements 416 within the set screw assembly and to electrical conductors within the proximal portion by, for example, resistance spot welding. Each of the plurality of connecting elements 410 can be individually insulated, such as with ETFE or other suitable materials. Arranging the connecting elements 410 in a spiral coil configuration along substantially the length of adapter 400 provides flexibility and reduces potential for strain or fatigue of connecting elements 410 during bending or twisting of adapter 400.

The middle portion 404 of the coil adapter 400 can be flexible, so as to enable bending of the coil adapter 400 to aid in an ideal positioning of the neurostimulator device relative to the stimulation lead within the body of a patient. In some embodiments, the coil adapter 400 can further include a flexible coating, which can serve to retain components of the coil adapter 400 in a fixed position relative to one another as well as to isolate the components from bodily fluids. For example, in one embodiment, the flexible coating can be a biocompatible over-molded silicone rubber, or similar such material.

It should be understood that various aspects disclosed herein may be combined in different combinations than the combinations specifically presented in the description and accompanying drawings. Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A neuromodulation adaptor configured to provide an electrical coupling between an otherwise incompatible stimulation lead and neurostimulator device, the neuromodulation adaptor comprising:
   a proximal portion including a plurality of electrical conductors spaced apart at a first pitch spacing and configured to electrically engage with a corresponding plurality of electrical terminals of a neurostimulator device; and
   a distal portion including a stimulation lead port assembly, the stimulation lead port assembly including an upper portion and a lower portion configured to house a plurality of connector elements and a set screw assembly, the plurality of connector elements and set screw assembly, spaced apart at a second pitch spacing and configured to electrically engage with a corresponding plurality of electrical connectors of a stimulation lead wherein the second pitch spacing is different than the first pitch spacing.

2. The neuromodulation adaptor of claim 1, wherein the set screw assembly includes a nonconductive set screw block, set screw and lower contact element.

3. The neuromodulation adaptor of claim 2, wherein the set screw assembly further includes an o-ring constructed of a non-electrically conductive, deformable polymer, positioned between the set screw and a portion of the set screw block.

4. The neuromodulation adaptor of claim 2, wherein the set screw assembly further includes one or more nubs configured to improve electrical contact between the lower contact element and the plurality of electrical connectors of a stimulation lead.

5. The neuromodulation adaptor of claim 2, wherein the set screw assembly further includes a spring contact configured to improve electrical contact between the lower contact element and the plurality of electrical connectors of a stimulation lead.

6. The neuromodulation adaptor of claim 1, wherein the upper portion of the stimulation lead port assembly is constructed of a nonconductive material.

7. The neuromodulation adaptor of claim 6, wherein a nonconductive set screw block of the set screw assembly and the upper portion of the stimulation lead port assembly are formed of a single unitary member.

8. The neuromodulation adaptor of claim 1, wherein the first pitch spacing is at least one of about 0.170 inches, about 0.085 inches, or about 0.080 inches (about 2 mm).

9. The neuromodulation adaptor of claim 1, wherein the second pitch spacing is at least one of about 0.170 inches, about 0.085 inches, or about 0.080 inches (about 2 mm).

10. The neuromodulation adaptor of claim 1, further comprising a flexible portion located between the proximal portion and the distal portion, configured to enable bending of the neuromodulation adaptor to aid in an ideal positioning of a neurostimulator device relative to a stimulation lead within a body of a patient.

11. The neuromodulation adaptor of claim 10, further comprising a plurality of insulated connecting elements coupled with and extending between the conductor elements and the electrical conductors, wherein the plurality of insulated connecting elements are arranged generally linearly through the flexible portion of the neuromodulation adaptor.

12. The neuromodulation adaptor of claim 11, wherein the set screw assembly includes a nonconductive set screw block, set screw and lower contact element.

13. The neuromodulation adaptor of claim 12, wherein a nonconductive set screw block of the set screw assembly and the upper portion of the stimulation lead port assembly are formed of a single unitary member.

14. The neuromodulation adaptor of claim 11, wherein the upper portion of the stimulation lead port assembly is constructed of a nonconductive material.

15. The neuromodulation adaptor of claim 11, wherein the first pitch spacing is at least one of about 0.170 inches, about 0.085 inches, or about 0.080 inches (about 2 mm).

16. The neuromodulation adaptor of claim 11, wherein the second pitch spacing is at least one of about 0.170 inches, about 0.085 inches, or about 0.080 inches (about 2 mm).

17. The neuromodulation adaptor of claim 10, further comprising a plurality of insulated connecting elements coupled with and extending between the conductor elements and the electrical conductors, wherein the plurality of insulated connecting elements are arranged in a spiral coil configuration through the flexible portion of the neuromodulation adaptor.

18. The neuromodulation adaptor of claim 17, wherein each of the plurality of insulated connecting elements in the distal portion of the neuromodulation adaptor are routed within channels of the set screw assembly for connection to respective conductor elements.

19. The neuromodulation adaptor of claim 17, wherein each of the plurality of insulated connecting elements are maintained in a spiral coil configuration through the distal portion of the neuromodulation adaptor until generally adjacent a respective conductor element.

20. The neuromodulation adaptor of claim 17, wherein the set screw assembly further includes an o-ring constructed of a non-electrically conductive, deformable polymer, positioned between the set screw and a portion of the set screw block.

21. The neuromodulation adaptor of claim 17, wherein the set screw assembly further includes one or more nubs configured to improve electrical contact between the lower contact element and the plurality of electrical connectors of a stimulation lead.

22. The neuromodulation adaptor of claim 17, wherein the set screw assembly further includes a spring contact configured to improve electrical contact between the lower contact element and the plurality of electrical connectors of a stimulation lead.

23. A neuromodulation adaptor configured to provide an electrical coupling between an otherwise incompatible stimulation lead and neurostimulator device, the neuromodulation adaptor comprising:
   a proximal portion including a plurality of electrical conductors spaced apart at a first pitch spacing; and
   a distal portion including a stimulation lead port assembly, the stimulation lead port assembly including an upper portion and a lower portion configured to house a plurality of connector elements and a set screw assembly, the plurality of connector elements and set screw assembly spaced apart at a second pitch spacing and configured to electrically engage with a corresponding plurality of electrical conductors of a previously implanted stimulation lead, wherein the second pitch spacing is different than the first pitch spacing.

24. A neuromodulation adaptor configured to provide an electrical coupling between an otherwise incompatible stimulation lead and neurostimulator device, the neuromodulation adaptor comprising:
   a proximal portion including a plurality of electrical conductors spaced apart at a first pitch spacing of at least one of about 0.085 inches or about 0.080 inches (about 2 mm) and is configured to electrically engage with a corresponding plurality of electrical terminals of a neurostimulator device; and
   a distal portion including a stimulation lead port assembly, the stimulation lead port assembly including a nonconductive upper portion and a lower portion configured to house a plurality of connector elements and a set screw assembly, the plurality of connector elements and set screw assembly spaced apart at a second pitch spacing of about 0.170 inches and is configured to electrically engage with a corresponding plurality of electrical conductors of a stimulation lead,
   wherein the set screw assembly includes a nonconductive set screw block, set screw, lower contact element, and o-ring constructed of a non-electrically conductive, deformable polymer, positioned between the set screw and a portion of the set screw block, wherein the set screw assembly further includes one or more nubs configured to improve electrical contact between the lower contact element and the plurality of electrical conductors of the stimulation lead.

* * * * *